United States Patent
Yamazaki et al.

(10) Patent No.: US 6,403,127 B1
(45) Date of Patent: *Jun. 11, 2002

(54) METHOD FOR PRODUCING NOODLES

(75) Inventors: Katsutoshi Yamazaki; Yutaka Nishimura, both of Kawasaki (JP)

(73) Assignee: Ajinomoto Co., Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/058,132

(22) Filed: Apr. 10, 1998

(30) Foreign Application Priority Data

Apr. 11, 1997 (JP) .............................. 9-108376

(51) Int. Cl.⁷ ................................ A21D 2/00
(52) U.S. Cl. ............................ 426/18; 426/28; 426/42; 426/44; 426/52
(58) Field of Search ................. 426/7, 18, 28, 426/42, 44, 48, 49, 52, 615, 518, 622

(56) References Cited

U.S. PATENT DOCUMENTS 5,156,956 A * 10/1992 Motoki et al. ............. 435/68.1
6,106,881 A * 8/2000 Yajima et al. ............. 426/549

FOREIGN PATENT DOCUMENTS

| JP | 49 37270 | 10/1974 |
| JP | A 61 119151 | 6/1986 |
| JP | B2 1 50382 | 10/1989 |
| JP | A 1 300889 | 12/1989 |
| JP | A 2 117353 | 5/1990 |
| JP | A 6 105662 | 4/1994 |
| JP | A 6 153832 | 6/1994 |
| WO | WO 93/15234 | 8/1993 |

OTHER PUBLICATIONS

Soeda et al., Japanese Patent Abstracts, abstracting JP 05–244887, Sep. 1993.*

Patent Abstracts of Japan, vol. 097, No. 002, Feb. 28, 1997, JP 08 256715, Oct. 8, 1996.

Patent Abstracts of Japan, vol. 096, No. 010, Oct. 31,1996, JP 08 149953, Jun. 11, 1996.

Derwent Abstracts, AN 96–174535, JP 08 051944, Feb. 27, 1996.

Patent Abstracts of Japan, vol. 018, No. 377 (C–1225), Jul. 15, 1994, JP 6 105662, Apr. 19, 1994.

* cited by examiner

*Primary Examiner*—Leslie Wong
(74) *Attorney, Agent, or Firm*—Oblon, Spivak, McClelland, Maier & Neustadt, P.C.

(57) ABSTRACT

A method for producing elastic and glutinous noodles is provided that includes adding transglutaminase and either gliadin or glutenin to cereal. The noodles keep their original elasticity and glutinosity for a long period of time, even after having been boiled and acid-processed or retorted. A composition and a dough mixture that include transglutaminase and gliadin or glutenin are also described.

14 Claims, No Drawings

METHOD FOR PRODUCING NOODLES

BACKGROUND OF THE INVENTION

1. Field of the Invention

The present invention relates to a method for producing noodles that includes adding transglutaminase and gliadin or glutenin to the dough mixture to enrich the taste, glutinosity and elasticity of the noodles produced. The noodles include, for example, Japanese wheat noodles, udon, soumen and hiyamugi made from wheat flour; Japanese buckwheat noodles, soba made from buckwheat flour; Chinese wheat noodles and coating of won-tons, shao-mais, jiaozies and the like made from wheat flour to which is added an alkali agent such as edible potassium carbonate; and spaghetti, macaroni and the like made from durum wheat flour. Noodles produced according to the method of the invention taste good and their glutinosity and elasticity last for a long period of time.

2. Description of the Related Art

Noodles include Chinese noodles, Japanese noodles of soba and udon, the coating of won-tons, shao-mais, jiaozies, and crispy spring rolls. These are sold in the market after having been processed to improve storability, for example, retorted, frozen, dried or semi-dried and acid-processed. Noodles should have a glutinous taste when eaten. However, the acid-processed or retorted noodles often lose the original taste and glutinosity of non-processed raw noodles. The processed noodles should have, after having been boiled, an elastic and especially glutinous taste for a long period of time.

Various improvements have been made in the field of processed noodles. For example, Japanese Patent Kokai 119151/1986 discloses a technique of adding vinegar along with seaweed extract, locust bean gum, guar gum, xanthane gum or the like to noodles. Japanese Patent Kokai 283547/1988 discloses a technique of coating boiled noodles with gelatin to protecting them from being non-glutinous and ensuring their good original shape. Japanese Patent Kokai 117353/1990 discloses a technique of adding a proteinaceous material, starch or the like along with active gluten, soybean protein, egg white, whole egg, casein, emulsifier, polysaccharide or the like to noodles. Japanese Patent Kokai 105662/1994 discloses a technique of adding a fraction from wheat consisting essentially of gliadin along with an ordinary noodle modifier such as egg white to noodles thereby improving the storability and processability of noodles. Japanese Patent Kokai 153832/1994 discloses a technique of adding a wheat fraction consisting essentially of glutenin to noodles to produce improved LL (long life) noodles. However, these techniques do not produce tasty noodles which can be stored for a long period of time, and further improvements in producing processed noodles are required.

Japanese Patent Kokai 105662/1994 and Japanese Patent Kokai 153832/1994 disclose a technique of using a gliadin fraction from wheat in producing noodles, in which the wheat fraction consisting essentially of gliadin is, along with egg white powder and other protein, added to noodles to improve the elasticity and glutinosity of the noodles. However, the noodles produced according to this technique were not satisfactorily elastic, stiff and glutinous, and inevitably become non-glutinous when boiled. Even though processed according to the disclosed technique, LL noodles that require heating and acid-processing after having been boiled lose their elasticity.

Apart from the techniques noted above, various methods of improving noodles with transglutaminase are known that do not satisfy the recent demand for elastic and glutinous noodles. In particular, if transglutaminase is added to processed noodles such as acid-processed noodles, retorted noodles and frozen noodles, these noodles easily lose their elasticity and glutinosity. Therefore, further improvements are required in adding transglutaminase to noodles.

Chinese noodles require toughness, elasticity and glutinosity, while Japanese udon noodles require elasticity and high glutinosity. More improvements in producing Chinese and Japanese noodles are required.

Transglutaminase is effective in stiffening noodles, since it acts on gluten in wheat flour to promote the crosslinking of gluten. As a result, transglutaminase can enhance the elasticity and glutinosity of noodles. However, the crosslinking network structure of gluten responsible for the strong elasticity and glutinosity of noodles that contain the crosslinked gluten is damaged when the noodles are processed with acid or retorted. As a result the noodles become rough and brittle and lose their intrinsic elasticity and glutinosity, and thus the noodles have an unpleasant taste.

SUMMARY OF THE INVENTION

The object of the present invention is to provide a method for producing noodles in which the noodles have improved elasticity, glutinosity and taste, and maintain their improved characteristics for a long period of time. Even when acid-processed, retorted and/or frozen, the noodles produced by the method of the invention maintain the good taste characteristics, toughness, stiffness and glutinosity for a long period of time.

Means for Solving the Problems

We, the present inventors have assiduously studied in order to attain the object, and, as a result, have found that when a combination of transglutaminase and gliadin or glutenin is added to noodles, the glutinosity and elasticity of the resulting noodles is improved. In particular, dry Japanese noodles according to the invention are not softened too much by drying and are much more glutinous. Thus, the dry noodles are tasty when boiled and eaten, like raw noodles. In acid-processing, retorting and/or freezing, Chinese noodles according to the invention do not lose their intrinsic taste yet are tough, elastic and glutinous for a long period of time. On the basis of these findings, we have completed the present invention.

Accordingly, the first embodiment of the present invention relates to a method for making noodles that includes:
  adding transglutaminase, and
  at least one of either gliadin or glutenin to a dough mixture that includes cereal.

The second embodiment of the present invention relates to a dough mixture that includes transglutaminase, at least one of either glutenin or gliadin, and cereal.

The third embodiment of the present invention relates to a noodle produced by a process that includes adding transglutaminase and at least one of either gliadin or glutenin to a dough mixture that includes cereal.

The fourth embodiment of the present invention relates to a composition that includes transglutaminase and at least one of either glutenin or gliadin.

BRIEF DESCRIPTION OF THE PREFERRED EMBODIMENTS

Various other objects, features and attendant advantages of the present invention will be more fully appreciated as the same becomes better understood from the following detailed description, which is not intended to be limiting unless otherwise specified.

The invention relates to the improvement in producing noodles from cereals and other side materials, which is characterized by adding transglutaminase along with gliadin or glutenin to the materials of noodles.

Transglutaminase is an enzyme for catalyzing the acyl transfer reaction of the γ-carboxyamide group of the glutamine residue in the peptide chain of wheat gluten. Acting as an acyl receptor on the ε-amino group of the lysine residue in protein, transglutaminase gives intramolecular and intermolecular ε-(γ-Glu)Lys bonds to protein molecules.

Transglutaminase may be either calcium-independent or calcium-dependent, any of which is usable in the invention. As examples of the former, mentioned are those derived from microorganisms (see, for example, Japanese Patent Kokai 27471/1989), the entire contents of which are hereby incorporated by reference. As examples of the latter, mentioned are those derived from guinea pig liver (see Japanese Patent Koukoku 50382/1989), fish-derived ones (see, for example, N. Seki et al's "Journal of the Fisheries Society of Japan", Vol. 56, pp. 125–132, 1990; and "Preprint of '90 Spring-term Discussions and Lectures in the Fisheries Society of Japan", page 219), and factor XIII existing in blood, etc. (see WO93/15234), the entire contents of each of which are hereby incorporated by reference. Apart from those, further mentioned are transglutaminases produced by genetic recombination (see Japanese Patent Kokai 300889/1989, Japanese Patent Kokai 199883/1993, Japanese Patent Kokai 225775/1994, and EP-0693556A) the entire contents of each of which are hereby incorporated by reference. Any of such transglutaminases is employable in the invention, without being limited by the sources and the production methods. Of those, however, preferred are calcium-independent ones in view of their functions for use in foods and of their economical aspects.

The amount of transglutaminase to be added is not particularly limiting and may be any ordinary one that is generally added to noodles for improving them. Preferable amounts may be from 0.1 to 100 units, but more preferably from 0.5 to 30 units, relative to 1 g of the protein content of the cereals. These ranges include all values and subranges therebetween. If the amount is smaller than the defined range, transglutaminase may be ineffective in improving the taste of noodles and in preventing the properties of noodles from being worsened during acid-processing or retorting. If so, the acid-processed or retorted noodles may be too soft. If the amount of the enzyme added is larger than the defined range, the taste of noodles may be worsened, and the noodles may be too tough.

Gliadin and glutenin are not particularly limiting and are referred to hereinunder. These are ethanol fractions from wheat gluten. Gliadin is a relatively small spherical protein having a molecular weight of from 30 kD to 80 kD, and this contributes to the glutinosity of noodles. In the invention, usable is any commercially-available gliadin, such as "Glia A" and "Glia AG" sold by Asama Chemicals Company. Any one as prepared from wheat gluten by known methods is also usable.

Glutenin is a thin fibrous protein having a molecular weight of from 200 kD to millions, and this contributes to the elasticity of wheat products. For this, usable is any commercially-available product, such as Asama Chemical's "Glute 100". Any one prepared from wheat gluten by known methods is also usable. Ethanol extraction of gliadin and glutenin from wheat protein is disclosed in, for example, "Journal of the Food Industry Association of Japan", Vol. 38, p. 477, 1991, the entire contents of which are hereby incorporated by reference. Briefly, gliadin and glutenin may be extracted from dough of soft flour or hard flour. These may be electrophoretically confirmed in Laemmli's SDS polyacrylamide gel electrophoresis (SDS-PAGE).

Japanese Patent Koukoku 37270/1974, the entire contents of which are hereby incorporated by reference, discloses a method for producing gum analogs through light thermal denaturation of wheat gluten. Baked gliadin as produced by this method is also usable in the invention. Molecules of baked gliadin have an enlarged hydrophobic area in their surface, while keeping their intrinsic properties. Therefore, baked gliadin acts favorably on noodles and improves their elasticity and glutinosity. Any ordinary baked gliadin is usable in the invention.

The amount of gliadin to be added is not particularly limiting and may be from 0.01 to 30.0% but is more preferably from 0.1 to 20.0%, relative to 100 g of the cereals. These ranges include all values and subranges therebetween. Unless otherwise specifically indicated, "%" referred to herein is by weight. If the amount is smaller than the defined range, the noodles may be. too tough and rough; but if it is larger than the same, the noodles may be too soft.

The amount of glutenin to be added is not particularly limiting and may preferably be from 0.01 to 30% but is more preferably from 0.1 to 25%, relative to 100 g of the cereals. These ranges include all values and subranges therebetween. If the amount is smaller than the defined range, the noodles may lose their intrinsic, smooth and glutinous taste. However, if it is larger than the defined range, the noodles may be too tough and brittle.

The cereal is not particularly limiting and may be any one ordinarily used in the art. Preferred examples include essential cereals such as rye flour, rice flour, soybean flour, soft flour, buckwheat flour, wheat flour, medium flour, hard flour, medium wheat flour, semi-hard wheat flour, durum semolina flour, and durum wheat flour, and mixtures thereof.

Egg white, processed starch and viscosity-increasing polysaccharides that are generally added to noodles are usable in the invention, without being specifically defined, so far as they do not interfere with the object of the invention. Their amounts are not specifically defined but may be any ordinary ones generally added to noodles.

In the invention, a composition that includes transglutaminase and gliadin or glutenin and optionally contains egg white, processed starch and viscosity-increasing polysaccharides may be added to the starting materials of noodles. Herein the invention provides a composition for producing noodles, which includes transglutaminase and gliadin or glutenin.

In carrying out the invention, transglutaminase and gliadin or glutenin are added to ordinary starting materials of noodles to make a dough mixture. If desired, any one or more of partial hydrolysates of protein, such as those of wheat protein, those of soybean protein, those of milk protein and those of gelatin, and other various proteins, such as milk protein, soybean protein and wheat protein, may be added to the dough mixture. Water and other ingredients may be added to and kneaded with the cereals such as wheat flour to prepare dough, during which step predetermined amounts of transglutaminase and gliadin or glutenin are added. The thus-kneaded dough may then be directly or after having been compounded and rolled, kept at a temperature between 0° C. and 650° C., preferably between 10° C. and 55° C., for a time of preferably 15 minutes to 24 hours, more preferably 50 minutes to 20 hours thereby making the enzyme, transglutaminase fully exhibit its enzymatic activity. These ranges include all values and subranges therebetween. During this aging, the enzyme, transglutaminase expresses its function.

Of the noodles produced by the method of the invention, non-processed raw noodles can be directly distributed in the market. If desired, the raw noodles may be boiled or steamed prior to being distributed. Also, the boiled or steamed noodles may be packaged and distributed. Also if desired, the raw noodles may be dried or semi-dried prior to being distributed. The boiled noodles may be processed with acid by dipping them in an acidic solution, or they may be retorted. The thus acid-processed or retorted noodles may then be distributed. Irrespective of their final forms mentioned above, the noodles produced by the method of the invention are elastic and glutinous and have a good taste all the time.

The activity unit of transglutaminase as referred to herein is defined and measured as follows. The enzyme is reacted with substrates of benzyloxycarbonyl-L-glutaminylglycine and hydroxylamine, then the resulting hydroxamic acid is formed into its iron complex in the presence of trichloroacetic acid, and the absorbance of the complex is measured at 525 nm. Based on the amount of the hydroxamic acid, a calibration curve is prepared, on which the enzymatic amount of transglutaminase capable of producing 1 μmol of hydroxamate within one minute is calculated. This is the activity unit, one unit of the enzyme, transglutaminase. For this, referred to is Japanese Patent Kokai 27471/1989, the entire contents of which are hereby incorporated by reference.

added per gram of the wheat protein in the flour used. The amount of gliadin therein is expressed as % for gliadin, when the flour used (2000 g) is defined as 100.

TABLE 1

| Dough Sample No, | Transglutaminase, U/g of protein | Gliadin, % |
| --- | --- | --- |
| Control No. 1 | 0 | 0 |
| Control No. 2 | 0 | 1.0 |
| Control No. 3 | 5 | 0 |
| Sample No. 1 of the Invention | 5 | 0.05 |
| Sample No. 2 of the Invention | 5 | 1.0 |
| Sample No. 3 of the Invention | 5 | 2.0 |

These raw noodles were boiled for 12 minutes and sensually tested by 10 specialists. In the tasting test, the boiled noodles were tried after having been stored for 30 minutes. The data are shown in Table 2, in which the elasticity, the glutinosity and the smoothness that indicate the taste of the noodles are ranked in 10 stages of from 1 to 10 points.

TABLE 2

| Dough Sample No. | Elasticity | Glutinosity | Smoothness | Total Evaluation | Profile Evaluation |
| --- | --- | --- | --- | --- | --- |
| Control No. 1 | 2 | 2.5 | 2 | 2.0 | Too tender and cut. |
| Control No. 2 | 2 | 3.5 | 3 | 2.8 | Too tender and cut. |
| Control No. 3 | 5 | 2.8 | 3 | 4.8 | Elastic but poorly glutinous. |
| Sample No. 1 of the Invention | 5.9 | 5.8 | 5.4 | 6.2 | Elastic and glutinous. |
| Sample No. 2 of the Invention | 6 | 7.0 | 6.5 | 7.3 | Glutinous and smooth. |
| Sample No.3 of the Invention | 7 | 8.0 | 7.0 | 8.6 | Very elastic and glutinous. |

EXAMPLES

Having generally described this invention, a further understanding can be obtained by reference to certain specific examples which are provided herein for purposes of illustration only and are not intended to be limiting unless otherwise specified.

Example 1

Japanese Noodles, udon 2000 g of medium wheat flour ("Kin-suzuran", by Nisshin Flour Milling) and 60 g of edible salt were dissolved in 920 g of water, to which was added a mixture of transglutaninase (relative activity: 1000 units/g) and gliadin as in Table 1 below. The resulting mixture was kneaded, using a noodle-making mixer (vacuum kneader, Tokyo Menki's TVMO3-0028 Model), under a reduced pressure of 500 mmHg for 7 minutes. Thus were prepared 6 samples of noodle dough. Each sample was roughly stirred, compounded and rolled, and thereafter kept at 20° C. for 60 minutes. Then, the obtained dough was cut, using a #12 cutter, into raw noodles having a final thickness of 2.5 mm. The amount of transglutamninase shown in Table 1 indicates units of the enzyme As compared with the controls Nos. 1 to 3, the samples Nos. 1 to 3 of the invention to which both transglutaminase and gliadin were added are much more elastic, glutinous and smooth and are better. The tasting test verifies that the samples Nos. 1 to 3 of the invention are much more favorably and much more glutinous than the controls Nos. 1 to 3. In particular, the samples Nos. 2 and 3 of the invention are extremely glutinous, and have high points of glutinosity and smoothness.

Example 2

Retorted Japanese Noodles, udon

The raw noodle samples prepared in Example 1 were boiled for 8 minutes, then immediately put into retortable pouches, and retorted at 125° C. for longer than 12 minutes (F0=6.8) to obtain 6 retorted noodle samples. The thus-retorted noodle samples were tried by 10 specialists in the same manner as in Example 1, and the data are shown in Table 3.

TABLE 3

| Dough Sample No. | Elasticity | Glutinosity | Smoothness | Total Evaluation | Profile Evaluation |
|---|---|---|---|---|---|
| Control No. 1 | 2 | 2 | 2 | 1.5 | Too much tender. |
| Control No. 2 | 2 | 3 | 2.8 | 2.5 | Much tender. |
| Control No. 3 | 4 | 2.5 | 3 | 3.8 | Much tender. |
| Sample No. 1 of the Invention | 5.1 | 5 | 5.1 | 5.0 | Elastic and smooth. |
| Sample No. 2 of the Invention | 5.5 | 5.5 | 5.5 | 5.5 | Elastic and smooth. |
| Sample No. 3 of the Invention | 6 | 7.5 | 6 | 7.0 | Elastic and very glutinous. |

Those retorted noodle samples were left overnight in a refrigerator at 10° C., and tried by specialists in the same manner as in Example 1. Like in Example 1, all the samples of the invention were evaluated good. This verifies that the noodles of the invention are, even after having been retorted, still satisfactorily elastic and glutinous.

Example 3

Chinese Noodles

To 2000 g of semi-hard wheat flour ("Toku-Number One", by Nisshin Flour Milling), added was a solution in 800 g of water of 20 g of edible salt, 10 g of powdery, edible potassium carbonate for noodles ("Funmatsu Kansui", by Nippon Colloid), gliadin-containing composition ("Glia A", by Asama Chemical), and transglutaminase derived from microorganisms of *Streptoverticillium mobaraense* OF 13819, as in Table 4. This was kneaded, using a mixer, at 76 rpm for 15 minutes. Then, by using a noodle-making machine (by Shinagawa Menki Seisaku-sho), this was roughly stirred, compounded and rolled into dough according to an ordinary manner. The resulting dough was kept at 200° C. for 60 minutes, and cut, using a #22 cutter, into raw Chinese noodles.

For comparison, a control sample No. 1 with no transglutaminase, a control sample No. 2 with neither transglutaminase nor gliadin (Asama Chemical's "Glia A"), and a control sample No. 3 with no gliadin were prepared in the same manner as above. The amounts of transglutaminase and gliadin added to the samples of the invention are shown in Table 4, in which the amount of transglutarinase indicates the number of units of the enzyme per gram of wheat protein in the flour used.

In Table 4, the amount of gliadin is expressed in-terms of % relative to the flour used (2000 g), which is defined as 100. Those five noodle samples were boiled for 2.5 minutes, and then kept in hot water at 90° C. for 30 minutes. These were tried for evaluating them. The results are shown in Table 5. The controls Nos. 1 to 3 were all too tender, and were not elastic but rough when eaten. As compared with these, it was verified that the samples Nos. 1 and 2 of the invention, to which were added both transglutaminase and gliadin, were more elastic, glutinous and smooth.

TABLE 4

| Dough Sample No. | Transglutaminase, U/g of protein | Gliadin, % |
|---|---|---|
| Control No. 1 | 0 | 0.3 |
| Control No. 2 | 0 | 0 |
| Control No. 3 | 5 | 0 |
| Sample No. 1 of the Invention | 5 | 0.3 |
| Sample No. 2 of the Invention | 10 | 1.0 |

Next, those five samples were boiled for 1 minute, then dipped in a solution of 0.75% lactic acid to have pH of lower than 4.2, put into retortable pouches, and sterilized under heat at 90° C. for 35 minutes. The thus-retorted samples were subjected to the same tasting test as above. Like the directly boiled samples, the retorted samples of the invention containing both transglutaminase and gliadin were the best. The tasting test was the same 10-point evaluation test as above. The data are shown in Table 6. The data of the retorted samples in Table 6 are nearly the same as those of the directly boiled samples in Table 5. Specifically, the controls Nos. 1 to 3 almost lost their elasticity and glutinosity, but the samples of the invention containing both transglutaminase and gliadin were still elastic, glutinous and smooth even after having been retorted. In the tasting test, each sample was evaluated by from 1 to 10 points.

TABLE 5

| Dough Sample No. | Elasticity | Glutinosity | Overall Texture | Profile Evaluation |
|---|---|---|---|---|
| Control No. 1 | 2 | 1.5 | 2 | Too tender. |
| Control No. 2 | 2 | 2 | 2.5 | Too tender, and not stiff |
| Control No. 3 | 4 | 2 | 2 | Too tender, and somewhat brittle. |
| Sample No. 1 of the Invention | 6 | 7 | 7 | Elastic, glutinous, and smooth. |
| Sample No. 2 of the Invention | 6.5 | 6 | 7 | Elastic, glutinous, and smooth. |

TABLE 6

| Dough Sample No. | Elasticity | Glutinosity | Overall Texture | Profile Evaluation |
|---|---|---|---|---|
| Control No. 1 | 2 | 1.5 | 2 | Too tender, and brittle. |
| Control No. 2 | 2 | 2 | 2.5 | Too tender, and not stiff |
| Control No. 3 | 2 | 2 | 2 | Too tender, and not smooth. |
| Sample No. 1 of the Invention | 6 | 6.3 | 6.5 | Elastic, glutinous, and smooth. |
| Sample No. 2 of the Invention | 6 | 5.9 | 6.5 | Elastic, glutinous, and smooth. |

Example 4

Coating of jiaozies

To 2000 g of semi-hard wheat flour ("Camellia", by Nisshin Flour Milling), added was a suspension in 660 g of water of 40 g of edible salt, and transglutaminase, glutenin, partial hydrolysate of wheat protein and sodium casein as in Table 7. This was kneaded, using the same noodle-making mixer (Tokyo Menki's vacuum kneader) as in Example 1, for 12 minutes. Thus were prepared four coating samples for jiaozies. These were kept at 25° C. for 20 minutes. Ingredients of jiaozies were wrapped with each coating sample to form jiaozies, which were then fried. The thus-fired jiaozies were tried by specialists.

In Table 7, the amount of transglutaminase indicates the number of units of the enzyme per gram of wheat protein in the flour used; the amounts of sodium casein and partial hydrolysate of wheat protein indicate their weight (g) per gram of wheat protein in the flour used; and the amount of gliadin is in terms of % relative to the flour used (2000 g) of being 100.

TABLE 7

| Dough Sample No. | Trans-glutaminase, U/g of protein | Glutenin, % | Partial Hydrolysate of Wheat Protein, g/g of protein | Sodium Casein, g/g of protein |
|---|---|---|---|---|
| Control No. 1 | 0 | 0 | 0 | 0 |
| Control No. 2 | 0 | 0.3 | 0.005 | 0.5 |
| Control No. 3 | 5 | 0 | 0 | 0 |
| Sample of the Invention | 5 | 0.3 | 0.005 | 0.5 |

As in Table 8 showing the results of the tasting test made by 10 specialists, all the control samples were too tender and brittle. As opposed to these, the sample of the invention was glutinous, soft and clear, and was the best as the coating of jiaozies. The tasting test was the same 10-point evaluation test as in Example 1.

TABLE 8

| Dough Sample No. | Glutinosity | Total Evaluation | Comments |
|---|---|---|---|
| Control No. 1 | 2.1 | 2 | Too tender and brittle. |
| Control No. 2 | 3.0 | 2.5 | Too tender. |
| Control No. 3 | 4.2 | 4.1 | Somewhat glutinous, but brittle. |

TABLE 8-continued

| Dough Sample No. | Glutinosity | Total Evaluation | Comments |
|---|---|---|---|
| Sample of the Invention | 6.2 | 6.5 | Glutinous, soft and clear. |

Example 5

Spaghetti 600 g of city water was added to 2000 g of durum semolina flour ("Reone B", by Nisshin Flour Milling), and kneaded for 10 minutes, using a pasta-making machine ("TYPE PM5", by Lucky Caffee Machine). This was immediately made into spaghetti dough having a predetermined length through extrusion-followed by cutting at a rate of 30 seconds/cutting. The durum semolina flour used herein was previously mixed with transglutaminase, gliadin and partial hydrolysate of wheat protein ("Glupearl 30", by Katayama Chemical Laboratory), as in Table 9.

For the amounts of transglutaminase, gliadin and partial hydrolysate of wheat protein in Table 9, referred to are the same as those in the above-mentioned Examples. The dough samples thus prepared were dried for 4 hours at a temperature of 35° C. and a humidity of 70%, using a constant temperature drier, to obtain dry spaghetti samples.

TABLE 9

| Dough Sample No, | Transglutaminase, U/g of protein | Gliadin, % | Partial Hydrolysate of Wheat Protein, g/g of protein |
|---|---|---|---|
| Control No. 1 | 0 | 0 | 0 |
| Control No. 2 | 0 | 0.04 | 0.05 |
| Control No. 3 | 10 | 0 | 0 |
| Sample of the Invention | 10 | 0.04 | 0.05 |

Each sample was boiled in boiling water for 8 minutes, and tried by 20 panelists. As in Table 10 showing the results of the tasting test, the controls Nos. 1 to 3 were all poor and only the sample of the invention containing both transglutaminase and gliadin was elastic and glutinous. The tasting test verifies that the sample of the invention is the best. The tasting test was the same 10-point evaluation test as above.

TABLE 10

| Dough Sample No. | Elasticity | Glutinosity | Total Evaluation | Comments |
|---|---|---|---|---|
| Control No. 1 | 3 | 3 | 1.5 | Tender. |
| Control No. 2 | 3.5 | 3.5 | 2.5 | Slightly glutinous, but brittle. |
| Control No. 3 | 4.8 | 4.5 | 3.8 | Glutinous, but somewhat brittle. |
| Sample of the Invention | 7.5 | 8 | 4.5 | Glutinous and good. |

Using the same ingredients as in Example 5, macaroni was prepared in an ordinary manner and tried. In the tasting test, the specialists gave the same data as in Example 5.

Reference Example 1

Sponge Cake 500 g of whole egg was added to 500 g of sugar and foamed for 5 minutes, using a Hobart mixer. Next, 500 g of soft flour and 10 g of baking powder (by Oriental Yeast) were, after having been sieved three times, mixed to give a uniform mixture. This was added to the previous mixture of egg and sugar and gently stirred. To this were added transglutaminase and gliadin, as in Table 11. Thus were prepared combination samples Nos. 1 and 2 containing both transglutarinase and gliadin, and controls Nos. 1 and 2 containing none of transglutaminase and gliadin or containing transglutaminase only.

TABLE 11

|  | Transglutaminase, U/g of protein | Gliadin, % |
| --- | --- | --- |
| Control No. 1 | 0 | 0 |
| Control No. 2 | 5 | 0 |
| Combination Sample No. 1 | 5 | 0.5 |
| Combination Sample No. 2 | 5 | 2 |

The data of those controls and combination samples are shown in Table 12. As in Table 12, the combination samples Nos. 1 and 2 were better than the controls Nos. 1 and 2, as being expanded more and being more tasty. The controls Nos. 1 and 2 expanded poorly to have a small volume, and were therefore hard and poorly tasty.

TABLE 12

|  | Specific Gravity of Dough (g/cc) | Specific Gravity of Expanded Cake (cc/g) | Taste of Cake | Feel of Cake |
| --- | --- | --- | --- | --- |
| Control No. 1 | 0.75 | 2.56 | Good | Hard |
| Control No. 2 | 0.82 | 2.39 | Good | Hard |
| Combination Sample No. 1 | 0.45 | 4.35 | Good | Soft |
| Combination Sample No. 2 | 0.36 | 4.55 | Good | Soft |

According to the present invention, transglutaminase is added, along with gliadin or glutenin, to an essential material of cereals and other side materials to produce noodles. The noodles thus produced are, even after having been boiled and thereafter acid-processed and/or retorted, still elastic, glutinous and smooth, and have a good taste. The processed noodles keep their good taste for a long period of time.

Having now fully described the invention, it will be apparent to one of ordinary skill in the art that many changes and modifications can be made thereto without departing from the spirit or scope of the invention as set forth herein.

This application is based on Japanese Patent Application 9-108376, filed Apr. 11, 1997, the entire contents of which are hereby incorporated by reference.

What is claimed as new and desired to be secured by Letters Patent of the United States is:

1. A method for making noodles, comprising:
adding transglutaminase, and
at least one of either extracted gliadin or extracted glutenin to a mixture comprising cereal flour to produce a dough mixture.

2. The method of claim 1, wherein said cereal flour comprises at least one essential cereal flour selected from the group consisting of rye flour, rice flour, soybean flour, soft flour, buckwheat flour, wheat flour, medium flour, hard flour, medium wheat flour, semi-hard wheat flour, durum semolina flour, and durum wheat flour, and mixtures thereof.

3. The method of claim 1, further comprising at least one step selected from the group consisting of mixing, kneading, aging, compounding, rolling, boiling, steaming, drying, acid-processing, retorting, extruding, and cutting, and combinations thereof.

4. The method of claim 1, further comprising adding water and mixing or kneading said dough mixture to obtain a dough.

5. The method of claim 4, further comprising compounding and rolling said dough.

6. The method of claim 4, further comprising aging said dough at a temperature of 0–60° C.

7. The method of claim 6, wherein said dough is aged at said temperature for a time of 15 minutes–24 hours.

8. The method of claim 1, wherein 0.1–100 units of transglutaminase are added to said mixture comprising cereal flour, relative to 1 g of protein in said cereal flour.

9. The method of claim 1, wherein 0.01–30% by weight of said gliadin or said glutenin is added, relative to 100 g of said cereal flour.

10. The method of claim 1, wherein said dough mixture further comprises at least one ingredient selected from the group consisting of egg, egg white, processed starch, viscosity-increasing polysaccharides, baking powder, salt, sugar, yeast, casein, protein, protein hydrolyzates, and water, and mixtures thereof.

11. A noodle, produced from the dough mixture prepared by the method of claim 1.

12. A noodle, produced by a process comprising:
adding transglutaminase, water, and
at least one of either extracted gliadin or extracted glutenin to a mixture comprising cereal flour to prepare a dough mixture;
mixing and kneading said dough mixture to obtain a dough; and
aging said dough at a temperature of 0–60° C. for a time of 15 minutes–24 hours.

13. The noodle of claim 12, comprising:
protein molecules having intramolecular and intermolecular $\epsilon(\gamma\text{-Glu})\text{Lys}$ bonds.

14. A method for making noodles of improved elasticity and/or glutinosity, comprising:
adding transglutaminase and
at least one of either extracted gliadin or extracted glutenin as additives to a mixture comprising cereal flour to produce a noodle dough mixture in an amount of said additives suitable for making noodles having the desired elasticity and for glutinosity.

* * * * *

UNITED STATES PATENT AND TRADEMARK OFFICE
CERTIFICATE OF CORRECTION

PATENT NO.  : 6,403,127 B1  Page 1 of 1
DATED       : June 11, 2002
INVENTOR(S) : Yamazaki et al.

It is certified that error appears in the above-identified patent and that said Letters Patent is hereby corrected as shown below:

Column 1,
Line 38, "protecting" should read -- protect --.

Column 7,
Line 38, "OF" should read -- IFO --;
Line 44, "200°" should read -- 20° --.

Column 10,
Line 16, "extrusion-followed" should read -- extrusion followed --.

Signed and Sealed this

Eighteenth Day of March, 2003

JAMES E. ROGAN
*Director of the United States Patent and Trademark Office*